(12) United States Patent
Zhang et al.

(10) Patent No.: US 10,370,376 B2
(45) Date of Patent: Aug. 6, 2019

(54) AMORPHOUS SUBSTANCE OF IDELALISIB AND PREPARATION METHOD THEREFOR

(71) Applicant: Alnova Pharmaceuticals, Ltd., Shanghai (CN)

(72) Inventors: Xini Zhang, Shanghai (CN); Zhigang Xiong, Shanghai (CN); Tao Hu, Shanghai (CN)

(73) Assignee: Alnova Pharmaceuticals, Ltd., Shanghai (CN)

( * ) Notice: Subject to any disclaimer, the term of this patent is extended or adjusted under 35 U.S.C. 154(b) by 0 days.

(21) Appl. No.: 15/783,207

(22) Filed: Oct. 13, 2017

(65) Prior Publication Data

US 2018/0037584 A1  Feb. 8, 2018

Related U.S. Application Data

(63) Continuation of application No. PCT/CN2016/079152, filed on Apr. 13, 2016.

(30) Foreign Application Priority Data

Apr. 15, 2015 (CN) .......................... 2015 1 0178885

(51) Int. Cl.
| | | |
|---|---|---|
| *C07D 473/34* | (2006.01) | |
| *A61K 31/52* | (2006.01) | |
| *A61P 29/00* | (2006.01) | |
| *A61P 35/00* | (2006.01) | |
| *A61P 37/00* | (2006.01) | |

(52) U.S. Cl.
CPC ............ *C07D 473/34* (2013.01); *A61P 29/00* (2018.01); *A61P 35/00* (2018.01); *A61P 37/00* (2018.01)

(58) Field of Classification Search
None
See application file for complete search history.

(56) References Cited

U.S. PATENT DOCUMENTS

2017/0260186 A1* 9/2017 Hu ...................... C07D 473/34

FOREIGN PATENT DOCUMENTS

| | | | |
|---|---|---|---|
| CN | 101031569 A | 9/2007 | |
| CN | 104130261 A | 11/2014 | |
| CN | 104262344 A | 1/2015 | |
| CN | 104334560 A | 2/2015 | |
| CN | 104892612 A | 9/2015 | |
| CN | 104892612 B | 12/2017 | |
| EP | 2612826 A2 | 7/2013 | |
| WO | 2013/134288 A1 | 9/2013 | |
| WO | 2015092810 A2 | 6/2015 | |
| WO | WO-2015092810 A2 * | 6/2015 | ........... C07D 473/34 |
| WO | WO-2016097314 A1 * | 6/2016 | ........... C07D 473/34 |
| WO | WO-2017175184 A1 * | 10/2017 | ........... C07D 239/00 |

OTHER PUBLICATIONS

Yu, L., Ed., Kwon Ick Chan, et al. "Amorphous Pharmaceutical Solids; Preparation, Characterization and Stabilization" Advanced Drug Delivery Rev, Elsevier, Amsterdam, NL Vo. 48, No. 1, May 16, 2001 (May 16, 2001), pp. 27-42, KP009065056, ISSN: 0169-409X, DOI: 10.1016/S0169-409X(01)00098-9.

* cited by examiner

*Primary Examiner* — Emily A Bernhardt
*Assistant Examiner* — Laura M Daniel
(74) *Attorney, Agent, or Firm* — Fox Rothschild LLP

(57) ABSTRACT

The present invention relates to an amorphous form of Idelalisib and its methods of preparation. Using a Cu-Kα radiation, the X-ray powder diffraction (XRPD) pattern does not contain sharp diffraction peaks at a diffraction angle expressed in degrees 2θ, and the X-ray powder diffraction pattern is shown in FIG. 1. The present invention also provides a preparation method for the amorphous form of Idelalisib. The amorphous form of Idelalisib of the present invention increases the solubility of Idelalisib and improves bioavailability of the drug product. As compared to the existing crystalline forms of Idelalisib, its solubility increases significantly, which improves body's absorption of the drug and makes it more efficacious in the clinical therapeutic treatment of diseases. Under the stress test conditions, the amorphous material can maintain good physical and chemical stabilities. The preparation method of amorphous Idelalisib according to the present invention is simple to operate and easy to implement.

12 Claims, 2 Drawing Sheets

AMORPHOUS SUBSTANCE OF IDELALISIB AND PREPARATION METHOD THEREFOR

CROSS-REFERENCE TO RELATED APPLICATIONS

This application is a Continuation of International Application No. PCT/CN2016/079152, filed Apr. 13, 2016, which in turn claims priority to Chinese Patent Application No. 201510178885.9, filed Apr. 15, 2015, the disclosures of both of which are hereby incorporated by reference in their entireties.

FIELD OF THE INVENTION

The current invention is related to an amorphous form of Idelalisib and its methods of preparation.

BACKGROUND OF THE INVENTION

Idelalisib has its chemical name as 5-fluoro-3-phenyl-2-[(1S)-1-(9H-purin-6-ylamino)propyl]-4(3H)-quinazolinone, and its structure is shown as formula (I):

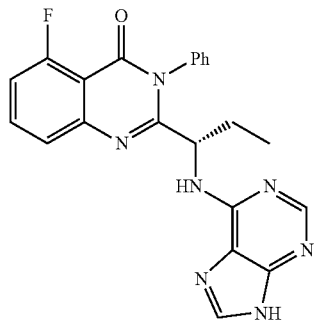

Formula (I)

Idelalisib (Brand Name as Zydelig) is a selective phosphoinositide 3-kinase δ (PI3K-δ, P110-δ) inhibitor developed by Gilead Sciences, Inc. On Jul. 23, 2014, US Food and Drug Administration (FDA) approved Idelalisib for three indications: relapsed chronic lymphocytic leukemia (CLL) in combination with rituximab, relapsed follicular B-cell non-Hodgkin lymphoma (FL) and relapsed small lymphocytic lymphoma (SLL) as a single prescription. The FDA has accelerated approval for the latter two, and patients have received at least two systemic treatments previously.

Idelalisib is the first oral, selective phosphoinositide 3-kinase δ (PI3K-δ, P110-δ) inhibitor that entered the market. P110-δ is involved in the change of the immune environment of B lymphocytes and plays a key role in the activation, proliferation, survival and migration of this type of tumor cells. The approval of Idelalisib brings a new option after Ibrutinib for the treatment of chronic lymphocytic leukemia. In the United States, the number of patients with chronic lymphocytic leukemia is second largest among adult patients with leukemia, and it is expected to increase more than 15,000 new patients in 2014. The development of new drugs for chronic lymphocytic leukemia, including Idelalisib and Ibrutinib, is expected to turn chronic lymphocytic leukemia from death sentences into a manageable chronic disease. Of course, the market for chronic lymphocytic leukemia has also grown, and the analyst of Bloomberg News forecast the market for chronic lymphocytic leukemia will soon climb to $9 billion.

U.S. Pat. No. 8,865,730 reported several polymorphs and solvates of Idelalisib, including Form I, Form II, Form III (mixed water and isopropanol solvate), Form IV (N,N-dimethylformamide solvate), Form V (dimethylsulfoxide solvate), and Form VII (mixed water and ethanol solvate). The polymorph in marketed Idelalisib Tablet is a mixture of Form I and Form II, and the dosages are 100 mg and 150 mg. As an antitumor drug, its dosage is relatively high, and other four polymorphs are solvate, which are not suitable for pharmaceutical use.

The solid form of drugs directly affects the solubility of active pharmaceutical ingredients, dissolution and bioavailability of formulation. In order to improve the bioavailability of drugs and reduce dosage and side effects, it is necessary to develop new solid forms of drug. Besides crystalline forms, solid forms of drugs can also be amorphous.

An amorphous form of drug is a special form of solid substance and has important application in preparation of drug. Current studies have shown that the amorphous form of many drugs have good stability and can be used in the development of general solid dosage form.

In addition, there are a few polyamorphous phenomena for drugs, and each amorphous form has different stability, and therefore searching for an amorphous form with good stability is also one of the ways to develop a better solid state of drugs.

DETAILED DESCRIPTION OF THE INVENTION

The present invention discloses an amorphous form of Idelalisib and its methods of preparation. The amorphous form is a new solid form of Idelalisib. It increases the solubility of Idelalisib and improves availability of formulation.

To achieve above goal, the present invention provides technology protocols as shown below:

An amorphous form of Idelalisib, using a Cu-Kα radiation, the amorphous Idelalisib is characterized by the X-ray powder diffraction pattern without sharp diffraction peaks at a diffraction angle expressed in degrees 2θ.

In one embodiment, the X-ray powder diffraction pattern has two broad peaks at a diffraction angle expressed in degrees between 2.0 and 50.0 degrees 2θ, and the X-ray powder diffraction is shown in FIG. 1.

The present invention provides a method for preparing the amorphous Idelalisib, comprising the following steps:
1) dissolving 5-fluoro-3-phenyl-2-[(1S)-1-(9H-purin-6-ylamino)propyl]-4(3H)-quinazolinone in solvent I to form a solution with concentration of 0.01~1 g/mL;
2) adding the solution obtained from step 1) to solvent II at temperature −80~100° C. to form a suspension, wherein solvent I is different from solvent II, and the volume ratio of the solution obtained from step 1) and solvent II is 1:1~200;
3) filtering the suspension formed in step 2), and drying the filter cake, to obtain amorphous 5-fluoro-3-phenyl-2-[(1S)-1-(9H-purin-6-ylamino)propyl]-4(3H)-quinazolinone.

In one embodiment, solvent I is selected from at least one of ether, halohydrocarbon, amide, sulfoxide or sulfone containing 8 or fewer carbons, and solvent II is selected from at least one of hydrocarbon, aromatic hydrocarbon, each with fewer than 8 carbons, or water.

The present invention provides another method for preparing the amorphous Idelalisib, comprising the following steps:
1) dissolving 5-fluoro-3-phenyl-2-[(1S)-1-(9H-purin-6-ylamino)propyl]-4(3H)-quinazolinone in an aqueous acid solution to form an acidic solution with concentration of 0.01~1 g/mL; wherein, the molar ratio of acid in an aqueous acid solution and 5-fluoro-3-phenyl-2-[(1S)-1-(9H-purin-6-ylamino)propyl]-4(3H)-quinazolinone is 1~20:1;
2) adding the acidic solution obtained in step 1) to an aqueous base solution, and adjusting pH value to not less than 10 at the temperature of −50~100° C., to form a suspension, the volume ratio of the aqueous acid solution and aqueous base solution is 1:1~100; wherein, the molar ratio of the base in the aqueous base solution and acid in the aqueous acid solution is 0.3~10:1;
3) filtering the suspension formed in step 2), and drying the filter cake, to obtain amorphous 5-fluoro-3-phenyl-2-[(1S)-1-(9H-purin-6-ylamino)propyl]-4(3H)-quinazolinone.

Further, the aqueous acid solution or aqueous base solution contains an organic solvent, and the organic solvent selected from at least one of water-miscible alcohol, ether, ketone or nitrile, each containing 8 or fewer carbons.

In one embodiment, the acid in the aqueous acid solution is selected from at least one of hydrochloric acid, sulfuric acid, alkyl sulfonic acid, aryl sulphonic acid, nitric acid, phosphoric acid or trifluoroacetic acid; the base in the aqueous base solution is selected from at least one of alkali metal hydroxide, alkali metal carbonate, alkali metal hydrogen phosphate or alkali metal phosphate.

The amorphous form of Idelalisib in the present invention is a new solid form of Idelalisib. The energy of intermolecular interaction is reduced in the crystalline substance due to the order and periodical arrangement of molecules, which results in relatively lower energy. In contrast, molecules in solid amorphous substance have higher energy than molecules in crystalline substance, so they disperse easily and increase solubility.

The amorphous state of the substance in the present invention has high dispersion. After forming the solid formulation, the dispersion of drug molecules is better and faster, which improves body's absorption of the drug. At the same time, compared to crystalline form, amorphous form is in a highly disordered state, and has higher surface free energy. Therefore, the solubility of amorphous form increases significantly, which improves body's absorption of the drug and makes it more efficient in the clinical treatment.

The advantageous effects of the present invention:

The solubility of amorphous Idelalisib of the present invention increases significantly, which improves body's absorption of the drug and makes it more efficient in the clinical treatment. Under the accelerated conditions (40±2° C., humidity 75%±5%), the amorphous material can maintain good physical stability and chemical stability. Thus, the present invention will have broad applications.

The preparation method of amorphous Idelalisib according to the present invention is simple to operate and easy to implement.

DETAILED DESCRIPTION OF THE INVENTION

The invention will be further described below with reference to specific examples. However, the scope of the invention is not limited by the examples included.

The X-ray powder diffraction patterns of the present invention were measured on Ultima IV X-ray diffractometer. The parameters of X-ray powder diffraction of the present invention are below:
X-ray powder parameter: Cu-Kα
Kα(Å): 1.5418
Voltage: 40 kilovolt
Electric current: 40 milliampere
Divergence slit: Auto
Scanning mode: Continuous
Scanning range: 2.0~60.0 degrees
Sampling step-length: 0.0200 degree
Scanning rate: 60 degrees/minutes Example 1

Figure 1:
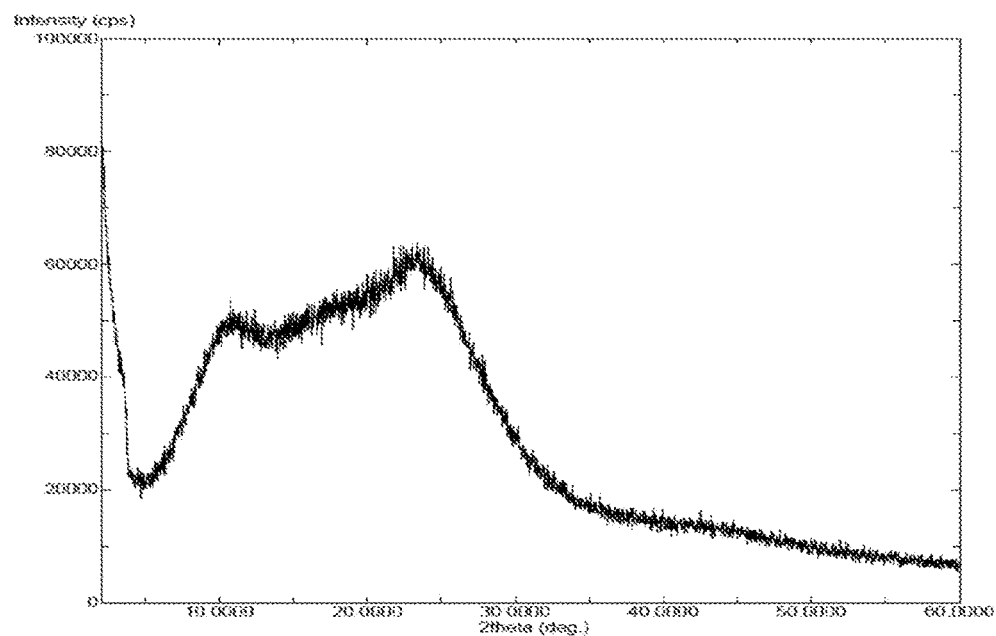
FIG. 1 shows X-ray powder diffraction pattern of amorphous Idelalisib in Example 1.

Idelalisib (50 milligrams) was suspended in tetrahydrofuran (750 microliters), and dissolved with stirring at room temperature. The above solution was added to n-heptane (10 microliters) pre-cooled to −25° C., and white solid precipitated with stirring, then 45 milligrams of solid was obtained after filtration and drying. The X-ray powder diffraction patterns was shown in FIG. 1, and the X-ray powder diffraction pattern does not contain sharp diffraction peaks at a diffraction angle expressed in degrees 2θ and has two broad peaks between 2.0 and 50.0 degrees 2θ.

Example 2

Figure 2:
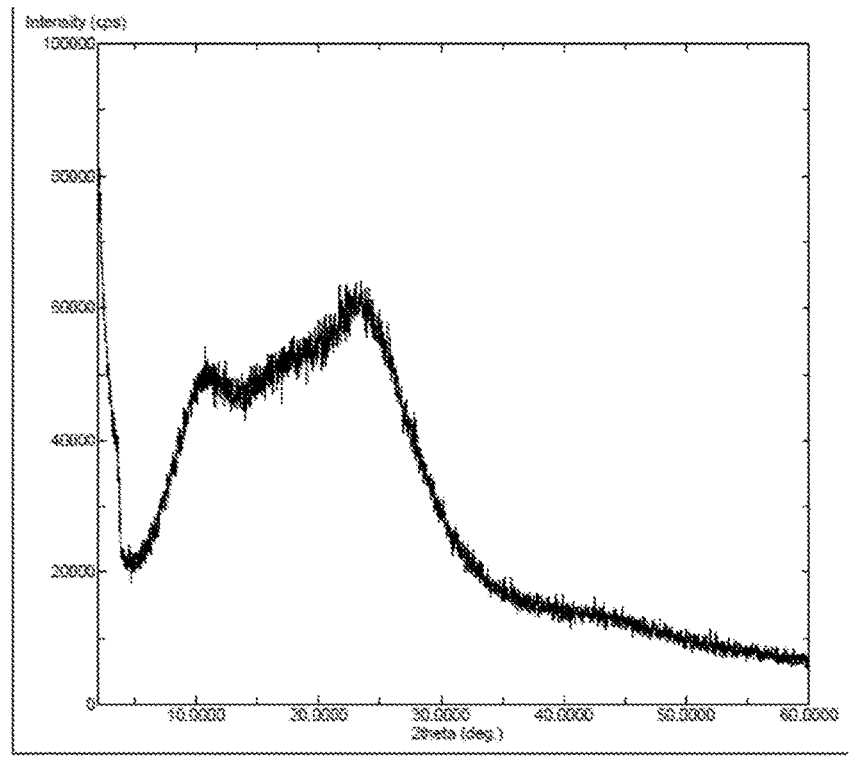
FIG. 2 shows X-ray powder diffraction pattern of amorphous Idelalisib in Example 2.

Idelalisib (50 milligrams) was suspended in dichloromethane (750 microliters), and dissolved with stirring at room temperature. The above solution was added to n-heptane (10 milliliters) pre-cooled to −80° C., white solid was precipitated with stirring, then 47 milligrams of solid was obtained after filtration and drying. The X-ray powder diffraction patterns was shown in FIG. 2, and the X-ray powder diffraction pattern does not contain sharp diffraction peaks at a diffraction angle expressed in degrees 2θ and has two broad peaks between 2.0 and 50.0 degrees 2θ.

Example 3

Idelalisib (30 milligrams) was suspended in N,N-dimethylformamide (90 microliters), and dissolved with stirring at room temperature. The above solution was added to water (450 microliters) pre-warmed to 80° C., white solid was precipitated with stirring, then 27 milligrams of solid was obtained as amorphous Idelalisib after filtration and drying.

Example 4

Figure 3:
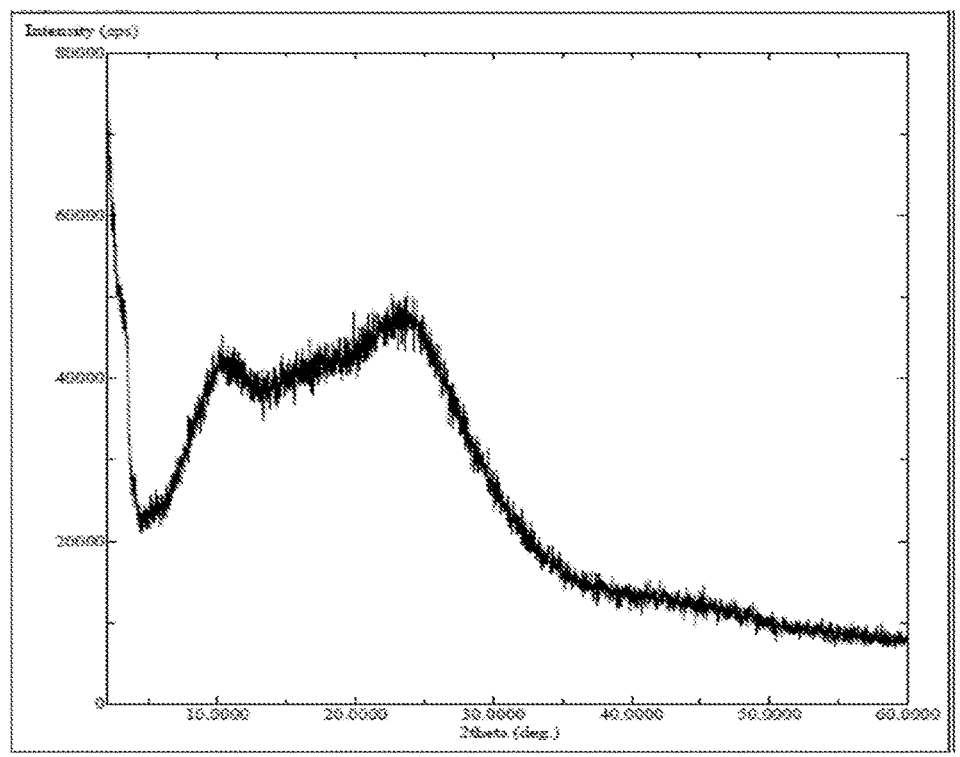
FIG. 3 shows X-ray powder diffraction pattern of amorphous Idelalisib in Example 4.

Idelalisib (30 milligrams) was suspended in methanol (300 microliters), and dissolved with stirring at room temperature. The above solution was added to water (1500 microliters), white solid was precipitated with stirring, then 23 milligrams of solid was obtained after filtration and drying. The X-ray powder diffraction patterns was shown in FIG. 3, and the X-ray powder diffraction pattern does not contain sharp diffraction peaks at a diffraction angle expressed in degrees 2θ and has two broad peaks between 2.0 and 50.0 degrees 2θ.

Example 5

Idelalisib (30 milligrams) was suspended in aqueous hydrochloride (1 molar/liter, 300 microliters), and dissolved with stirring at room temperature. The above solution was added to aqueous sodium hydroxide (1 molar/liter, 600 microliters), white solid was precipitated with stirring, then 24 milligrams of solid was obtained as amorphous Idelalisib after filtration and drying.

Example 6

Idelalisib (30 milligrams) was suspended in aqueous hydrochloride (1 molar/liter, 300 microliters), and dissolved with stirring at room temperature. The above solution was added to aqueous sodium hydroxide (1 molar/liter, 600 microliters) warmed to 80° C., white solid was precipitated with stirring, then 24 milligrams of solid was obtained as amorphous Idelalisib after filtration and drying.

Example 7

Idelalisib (30 milligrams) was suspended in aqueous hydrochloride (1 molar/liter, 200 microliters), and dissolved with stirring at room temperature. The above solution was added to the mixture of aqueous sodium hydroxide (1 molar/liter, 300 microliters) and methanol (300 microliters) pre-cooled to −80° C., white solid was precipitated with stirring, then 22 milligrams of solid was obtained as amorphous Idelalisib after filtration and drying.

Example 8: The Comparison of Apparent Solubility for Amorphous Idelalisib and Crystalline Idelalisib (Form I)

The amorphous Idelalisib was prepared according to the method of Example 1. The crystalline Idelalisib, Form I, was prepared according to the method of Example 1 of U.S. Pat. No. 8,865,730.

Determination of apparent solubility: weigh a certain amount of the sample into a 1.8 mL of centrifuge tube, add 1 mL of the specified pH diluent, cap tightly. Each solution was prepared with 3 replicates (the amount of the added sample must be much larger than of which can be formed a saturated solution at different pH, details were shown in Table 1), and then 1 mL of the designated pH diluent was added. Then the centrifuge tube containing the test solution was shaken in a water bath at 37° C.±0.5° C. for 12 hours, let Stand in an oven at 37° C. for 2 hours. The upper lay was filtered through a 0.45 m microporous membrane. Pipette 200 uL of the filtrated solution into a vial containing 200 uL of acetonitrile, shaken to mix. Label it as test solution. Inject 2 uL of the test solution to HPLC system, record the peak area of main peak. Inject the reference standard solution following the same procedure as the test solution, record the peak area of the main peak of reference standard. According to the main peak area of the test solution and the reference solution, the concentration of the reference solution and the concentration of the test solution are calculated by external standard method. Then the saturation solubility will be obtained by multiplying concentration by the dilution factor of 2. The final result of saturation solubility is the average result of three parallel test samples.

Preparation of reference standard solution: accurately weight about 25 mg of Idelalisib (Form I) into a 25 mL of volumetric flask, dissolve and dilute to the volume with diluent (acetonitrile:water=1:1). The concentration of the reference standard is about 1 mg/mL.

Preparation of Diluents of Different pH:

(1) pH=1.0 diluent: Add 9 mL of concentrated HCl to a 1000 mL of volumetric flask, diluted to the volume with water.

(2) pH=2.0 diluent: Solution A: Transfer 16.6 mL of phosphoric acid to a 100 mL volumetric flask, dilute to the volume with water, shake to mix. Solution B: Weigh and transfer 71.63 g of sodium disodium phosphate to a 1000 mL of volumetric flask, dilute to the volume with water, dissolve and mix well. Mix 72.5 mL of solution A and 27.5 mL of solution B.

(3) pH=3.0 diluent: transfer 50 mL of glacial acetic acid to a 1000 mL of volumetric flask, add 800 mL of water, adjust pH to 3.0 with lithium hydroxide, then diluted to the volume with water.

(4) pH=4.0 diluent: weigh and transfer 7.7 g of ammonium acetate, dissolve with 50 mL of water, add 6 mL of glacial acetic acid, then diluted to 100 mL with water.

(5) pH=5.6 diluent: Phthalate buffer (pH 5.6): Transfer 10 g of potassium hydrogen phthalate, add 900 mL of water, stir to dissolve, adjust pH to 5.6 with sodium hydroxide solution (or diluted hydrochloric acid if necessary) then diluted to the volume with water.

(6) pH=6.8 diluent: mix 250 mL of 0.2 mol/L potassium dihydrogen phosphate solution and 118 mL of 0.2 mol/L sodium hydroxide solution, diluted to 1000 mL with water, shaken to mix.

(7) pH=7.4 diluent: transfer 1.36 g of potassium dihydrogen phosphate, add 79 mL of 0.1 mol/L sodium hydroxide solution, diluted to 200 mL with water.

TABLE 1

| pH | Addition of amorphous Idelalisib (mg) | Addition of crystalline Idelalisib (Form I) (mg) |
|---|---|---|
| 1.0 | 80 | 80 |
| 2.0 | 20 | 20 |
| 3.0 | 20 | 20 |
| 4.5 | 20 | 20 |
| 5.6 | 20 | 20 |
| 6.8 | 20 | 20 |
| 7.4 | 20 | 20 |

The experiment results of comparison are shown in Table 2:

TABLE 2

| pH | Apparent solubility of test sample (ug/mL) | Apparent solubility of reference standard (ug/mL) |
|---|---|---|
| 1.0 | 52686.67 | 34580.16 |
| 2.0 | 7037.94 | 1756.55 |
| 3.0 | 1622.95 | 317.47 |
| 4.5 | 694.19 | 147.02 |
| 5.6 | 75.75 | 46.91 |
| 6.8 | 75.31 | 47.35 |
| 7.4 | 74.31 | 45.08 |

Table 2 shows that the apparent solubility of the amorphous Idelalisib is significantly higher than that of the Form I at each pH.

Example 9: Impact Factor Test of the Amorphous Idelalisib

Material: Amorphous Idelalisib was prepared according to the method of Example 1

Experiment conditions: temperature 40° C.±2° C., humidity 75%±5%

The substance was detected by HPLC.

The experiment results of impact factor test are shown in Table 3.

TABLE 3

| Detection Item | Time | Experiment conditions | | | |
| --- | --- | --- | --- | --- | --- |
| | | Temperature 40° C. ± 2° C. | Temperature 60° C. ± 2° C. | Humidity 75% ± 5% | Humidity 90% ± 5% |
| Relevant substances (Total impurities %) | 0 day | | 0.12 | | |
| | 5 days | 0.13 | 0.14 | 0.14 | 0.16 |
| | 10 days | 0.14 | 0.16 | 0.14 | 0.16 |
| Crystalline (XRPD) | 0 day | There is no peak of crystalline Idelalisib after deducting the background of medicinal excipient | | | |
| | 5 days | There is no peak of crystalline Idelalisib after deducting the background of medicinal excipient | | | |
| | 10 days | There is no peak of crystalline Idelalisib after deducting the background of medicinal excipient | | | |

Table 3 shows that there is no significant changes in the relevant substances of amorphous Idelalisib and no crystallization of Idelalisib was observed in the conditions of high temperature, high humidity after 10 days.

Example 10: Accelerated Stability Test of the Amorphous Idelalisib

Material: amorphous Idelalisib was prepared according to the method of Example 1.

Experiment conditions: temperature 40° C.±2° C., humidity 75%±5%

The substance was detected by HPLC.

The experiment results of accelerate stability test are shown in Table 4.

TABLE 4

| Detection Item | Time | Experiment conditions Temperature 40° C. ± 2° C., Humidity 75% ± 5% |
| --- | --- | --- |
| Relevant substances (Total impurities %) | 0 month | 0.12 |
| | 1 month | 0.14 |
| | 2 months | 0.15 |
| | 3 months | 0.16 |
| | 6 months | 0.19 |
| Crystalline (XRPD) | 0 month | There is no peak of crystalline Idelalisib after deducting the background of medicinal excipient |
| | 1 month | There is no peak of crystalline Idelalisib after deducting the background of medicinal excipient |
| | 2 months | There is no peak of crystalline Idelalisib after deducting the background of medicinal excipient |
| | 3 months | There is no peak of crystalline Idelalisib after deducting the background of medicinal excipient |
| | 6 months | There is no peak of crystalline Idelalisib after deducting the background of medicinal excipient |

Table 4 shows that there is no significant changes in the relevant substances of amorphous Idelalisib and no crystallization of Idelalisib was observed in the accelerated test conditions after 6 months.

The amorphous Idelalisib of the present invention increases the solubility of Idelalisib significantly and improves bioavailability of the drug, which makes it more efficient in the clinical treatment. Under the stress test condition (40±2° C., humidity 75%±5%), the amorphous material can maintain good physical stability and chemical stability.

The invention claimed is:

1. A method for preparing an amorphous form of Idelalisib, comprising the steps of:
   1) dissolving 5-fluoro-3-phenyl-2-[(1S)-1-(9H-purin-6-ylamino)propyl]-4(3H)-quinazolinone in a solvent I selected from the group consisting of ether, halohydrocarbon, alcohol, amide, sulfoxide, and sulfone, each containing 8 or fewer carbons, to form a solution with a concentration of 0.01 to 1 g/ml;
   2) adding the solution obtained from step 1) to a solvent II selected from hydrocarbons at temperature −80 to 100° C. to form a suspension, wherein the volume ratio of the solution obtained from step 1) and solvent II is 1:1 to 200; and
   3) filtering the suspension formed in step 2) and drying the filter cake to obtain the amorphous form of 5-fluoro-3-phenyl-2-[(1S)-1-(9H-purin-6-ylamino)propyl]-4(3H)-quinazolinone.

2. A method for preparing an amorphous Idelalisib, comprising:
   1) dissolving 5-fluoro-3-phenyl-2-[(1S)-1-(9H-purin-6-ylamino)propyl]-4(3H)-quinazolinone in an aqueous acid solution to form an acidic solution with a concentration of 0.01 to 1 g/ml; wherein molar ratio of the acid and 5-fluoro-3-phenyl-2-[(1S)-1-(9H-purin-6-ylamino)propyl]-4(3H)-quinazolinone in the aqueous acid solution is 1 to 20:1;
   2) adding the acidic solution obtained in step 1) to an aqueous base solution, and adjusting pH value to not less than 10, at the temperature of −50 to 100° C., to form a suspension, the volume ratio of the acidic solution and the aqueous base solution is 1:1 to 100; wherein, the molar ratio of the base in the aqueous base solution and the acid in the aqueous acid solution is 0.3 to 10:1; and
   3) filtering the suspension formed in step 2), and drying the filter cake, to obtain amorphous 5-fluoro-3-phenyl-2-[(1S)-1-(9H-purin-6-ylamino)propyl]-4(3H)-quinazolinone.

3. The method of claim 2, wherein the aqueous acid solution or the aqueous base solution comprises an organic solvent, and the organic solvent is selected from at least one of water-miscible alcohol, ether, ketone, and nitrile, each containing 8 or fewer carbons.

4. The method of claim 2, wherein the acid in the aqueous acid solution is selected from at least one of hydrochloric acid, sulfuric acid, alkyl sulfonic acid, aryl sulfonic acid, nitric acid, phosphoric acid, and trifluoroacetic acid.

5. The method of claim 2, wherein the base in the aqueous base solution is selected from at least one of alkali metal hydroxide, alkali metal carbonate, alkali metal hydrogen phosphate, and alkali metal phosphate.

6. The method of claim 3, wherein the acid in the aqueous acid solution is selected from at least one of hydrochloric acid, sulfuric acid, alkyl sulfonic acid, aryl sulfonic acid, nitric acid, phosphoric acid, and trifluoroacetic acid.

7. The method of claim 3, wherein the base in the aqueous base solution is selected from at least one of alkali metal hydroxide, alkali metal carbonate, alkali metal hydrogen phosphate, and alkali metal phosphate.

8. A method for preparing an amorphous form of Idelalisib, comprising the steps of:
1) dissolving 5-fluoro-3-phenyl-2-[(1S)-1-(9H-purin-6-ylamino)propyl]-4(3H)-quinazolinone in a solvent I selected from the group consisting of ether, halohydrocarbon, alcohol, amide, sulfoxide, and sulfone, each containing 8 or fewer carbons, to form a solution with a concentration of 0.01 to 1 g/ml;
2) adding the solution obtained from step 1) to a solvent II selected from hydrocarbons at temperature −80 to 100° C. to form a suspension, wherein the volume ratio of the solution obtained from step 1) and solvent II is 1:1 to 200;
3) filtering the suspension formed in step 2) and drying the filter cake to obtain the amorphous form of 5-fluoro-3-phenyl-2-[(1S)-1-(9H-purin-6-ylamino)propyl]-4(3H)-quinazolinone.

9. The method of claim 8, wherein the solvent I is selected from the group consisting of dichloromethane, tetrahydrofuran, N,N,-dimethylformamide, and methanol.

10. The method of claim 8, wherein the solvent II is selected from the group consisting of hexanes, heptanes, octanes, and water.

11. The method of claim 1, wherein the solvent I is selected from the group consisting of dichloromethane, tetrahydrofuran, N,N,-dimethylformamide, and methanol.

12. The method of claim 1, wherein the solvent II is selected from the group consisting of hexanes, heptanes, octanes, and water.

* * * * *